(12) United States Patent
Rendschmidt et al.

(10) Patent No.: US 12,399,602 B2
(45) Date of Patent: Aug. 26, 2025

(54) METHOD FOR PROVIDING A FAVORITE MENU ON A COMPUTING DEVICE AND A COMPUTING DEVICE

(71) Applicant: Roche Diabetes Care, Inc., Indianapolis, IN (US)

(72) Inventors: Til Rendschmidt, Wiesbaden (DE); Itzhak Grinberg, Haifa (IL)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 558 days.

(21) Appl. No.: 16/096,357

(22) PCT Filed: Apr. 28, 2017

(86) PCT No.: PCT/EP2017/060173
§ 371 (c)(1),
(2) Date: Oct. 25, 2018

(87) PCT Pub. No.: WO2017/191045
PCT Pub. Date: Nov. 9, 2017

(65) Prior Publication Data
US 2019/0129579 A1    May 2, 2019

(30) Foreign Application Priority Data
May 3, 2016 (EP) .................................. 16168117

(51) Int. Cl.
*G06F 3/0482* (2013.01)
*A61M 5/172* (2006.01)
(Continued)

(52) U.S. Cl.
CPC ........... *G06F 3/0482* (2013.01); *A61M 5/172* (2013.01); *G06F 3/0481* (2013.01); *G16H 20/17* (2018.01);
(Continued)

(58) Field of Classification Search
CPC ........ G16H 10/60; G16H 50/20; G16H 10/20; G16H 50/70; G16H 20/13; G16H 20/30;
(Continued)

(56) References Cited

U.S. PATENT DOCUMENTS 5,724,985 A * 3/1998 Snell ........................ A61N 1/08
600/510
7,685,026 B1 * 3/2010 McGrady ............... G06Q 10/08
705/28
(Continued)

FOREIGN PATENT DOCUMENTS

CN  103226647  7/2013
CN  103250158  8/2013
(Continued)

OTHER PUBLICATIONS

Office Action in related KR10-2018-7032010 issued Jun. 24, 2020.

*Primary Examiner* — Toan H Vu
(74) *Attorney, Agent, or Firm* — Woodard, Emhardt, Henry, Reeves & Wagner, LLP

(57) ABSTRACT

The disclosure relates to a method for providing a favorite menu on a computing device (30), the method comprising steps of: providing (1) an item, wherein at least one action is assigned to the item, storing (2; 12; 21) the item in a favorite list, and displaying (3; 13; 22) the favorite list on a display device (33) of the computing device (30), wherein the item is provided based on a medical selection criterion. Further, a computing device (30) comprising a processor (31), a memory (32) and a display device (33) is disclosed. (FIG. 1).

7 Claims, 3 Drawing Sheets

Figure 1:
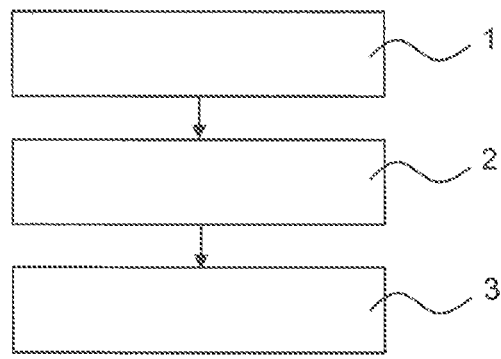

(51) Int. Cl.
  *G06F 3/0481* (2022.01)
  *G16H 20/17* (2018.01)
  *G16H 20/60* (2018.01)
  *G16H 40/63* (2018.01)
  *G16H 50/30* (2018.01)
(52) U.S. Cl.
  CPC .............. *G16H 20/60* (2018.01); *G16H 40/63* (2018.01); *G16H 50/30* (2018.01); *A61M 2205/502* (2013.01); *A61M 2205/505* (2013.01)
(58) Field of Classification Search
  CPC ........ G16H 20/17; G16H 50/30; G16H 40/63; G06F 19/00; G06F 19/321; G06F 19/328; G06F 19/325; G06F 3/0482; G06F 16/93; G06F 3/0481; G06F 3/04842; G06F 19/3481; G06F 16/00; G06F 16/24; G06F 16/245; G06F 16/338; G06F 16/951; G06F 19/3468; G06F 16/20; G06F 16/248; G06F 16/5866; G06F 17/2705; G06F 19/32; G06F 3/0488; G06F 19/3418; G06F 13/102; G06F 19/3456; G06F 19/3475; G06F 3/04817; G06F 3/04847; A61B 5/14532; A61B 5/742; A61B 5/746; A61M 5/172; A61M 2205/502; A61M 2205/505
  See application file for complete search history.

(56) References Cited

U.S. PATENT DOCUMENTS

| | | | | |
|---|---|---|---|---|
| 8,645,865 B2* | 2/2014 | Ananian | ............... | G06F 3/0482 715/834 |
| 8,821,433 B2* | 9/2014 | Blomquist | ............. | G16H 20/17 604/66 |
| 8,849,458 B2* | 9/2014 | Weinert | ................. | G16H 15/00 700/266 |
| 9,008,803 B2* | 4/2015 | Blomquist | ............. | G16H 50/20 700/17 |
| 9,662,438 B2* | 5/2017 | Kamen | ............. | A61M 5/14244 |
| 9,833,177 B2* | 12/2017 | Blomquist | .......... | G06F 19/3468 |
| 9,847,038 B2* | 12/2017 | Mayou | .................... | A61B 5/165 |
| 10,016,561 B2* | 7/2018 | Saint | ........................ | G16H 40/63 |
| 10,022,498 B2* | 7/2018 | Ruchti | ................. | A61M 5/1723 |
| 10,049,768 B2* | 8/2018 | Blomquist | .......... | G06F 19/3468 |
| 10,194,319 B2 | 1/2019 | Kim et al. | | |
| 10,242,060 B2* | 3/2019 | Butler | ................... | G06Q 10/06 |
| 10,252,002 B2* | 4/2019 | Haider | ................. | G16H 40/63 |
| 2003/0036927 A1 | 2/2003 | Bowen | | |
| 2003/0069759 A1* | 4/2003 | Smith | ................... | G06F 19/328 705/3 |
| 2004/0121295 A1* | 6/2004 | Stuart | .................... | G09B 23/28 434/262 |
| 2004/0186746 A1* | 9/2004 | Angst | ................. | G06F 21/6245 705/3 |
| 2005/0022274 A1* | 1/2005 | Campbell | ............. | G16H 40/67 D24/100 |
| 2005/0137530 A1* | 6/2005 | Campbell | .......... | A61M 5/14244 604/131 |
| 2006/0252998 A1* | 11/2006 | Kimbrell | ............. | G08B 25/016 600/300 |
| 2008/0065420 A1* | 3/2008 | Tirinato | .................. | G06Q 50/24 705/3 |
| 2009/0147011 A1 | 6/2009 | Buck et al. | | |
| 2009/0150758 A1* | 6/2009 | Gejdos | ................... | G16H 15/00 715/200 |
| 2009/0217189 A1* | 8/2009 | Martin | ................... | G16H 10/60 715/772 |
| 2009/0240120 A1* | 9/2009 | Mensinger | ............. | G16H 40/63 600/301 |
| 2010/0064374 A1* | 3/2010 | Martin | ................... | G16H 40/63 726/27 |
| 2010/0083164 A1* | 4/2010 | Martin | ................... | G16H 40/63 715/781 |
| 2010/0198142 A1* | 8/2010 | Sloan | ............... | G01N 33/48792 604/66 |
| 2011/0081888 A1* | 4/2011 | Waniss | ............. | H04M 1/72527 455/411 |
| 2011/0092788 A1* | 4/2011 | Long | ...................... | G16H 40/63 600/365 |
| 2011/0124996 A1* | 5/2011 | Reinke | ................. | G06F 19/3456 600/365 |
| 2011/0179389 A1* | 7/2011 | Douen | .................... | G09B 23/28 715/843 |
| 2011/0184752 A1* | 7/2011 | Ray | ........................ | G16H 15/00 705/2 |
| 2012/0095310 A1* | 4/2012 | Long | ...................... | G16H 40/63 600/365 |
| 2012/0266251 A1* | 10/2012 | Birtwhistle | ......... | G06F 19/3481 726/26 |
| 2012/0289802 A1* | 11/2012 | Bousamra | .......... | A61B 5/14532 600/365 |
| 2013/0042117 A1* | 2/2013 | Birtwhistle | ......... | H04L 63/0823 713/182 |
| 2013/0164718 A1* | 6/2013 | Buck | ...................... | G16H 20/60 434/127 |
| 2013/0172707 A1* | 7/2013 | Galley | ................ | G06F 19/3468 600/365 |
| 2014/0088393 A1* | 3/2014 | Bernstein | ............... | G16H 20/00 600/365 |
| 2014/0188398 A1* | 7/2014 | Cohen | .................... | A61B 5/746 702/19 |
| 2014/0379360 A1* | 12/2014 | Berven | ............... | G06F 19/3456 705/2 |
| 2015/0120482 A1* | 4/2015 | Kourpas | ............. | G06Q 30/0605 705/26.2 |
| 2017/0038951 A1* | 2/2017 | Reicher | ................. | G06F 16/245 |
| 2017/0173261 A1* | 6/2017 | O'Connor | .......... | A61M 5/14248 |
| 2018/0197628 A1* | 7/2018 | Wei | .................... | A61B 5/14532 |
| 2019/0381243 A1* | 12/2019 | Bowland | ............. | A61M 5/1723 |

FOREIGN PATENT DOCUMENTS

| | | |
|---|---|---|
| CN | 105160199 | 12/2015 |
| KR | 10-2010-0008945 | 1/2010 |
| KR | 10-2012-0125086 | 11/2012 |
| WO | WO 2010/029551 | 3/2010 |

* cited by examiner

METHOD FOR PROVIDING A FAVORITE MENU ON A COMPUTING DEVICE AND A COMPUTING DEVICE

The present disclosure refers to a method for providing a favorite menu on a computing device and a computing device.

BACKGROUND

Even if modern insulin pumps offer a variety of advanced features to adapt insulin delivery to a patient lifestyle, those features are often used rarely in daily routine. One reason might be missing education. Another reason may be that those advanced features usually demand additional logical steps, screens and user inputs which make the use complicated and add burden to daily diabetes routine. Burden should be minimized as much as possible in order to avoid loss of motivation, bad glucose control, worsening of distress and even depression. Basic and advanced features cannot be standardized with regard to individual patient requirements because the requirements can change with more or less active life style, special situations, age, diabetes duration etc.

Document WO 2010/029551 A2 discloses a method for dispensing a therapeutic fluid to the body of a patient according to a meal type. To determine a bolus delivery a meal type and a content of a dietary intake to be consumed by the patient are received. Then a bolus delivery pattern corresponding to the meal type is retrieved from a memory and a bolus amount of the therapeutic fluid corresponding to the content of the intake is determined, which is dispensed. Furthermore, the method for providing a suitable bolus delivery pattern can be based on re-establishing tailored bolus profiles, for example, by comparing a user's bG responses (bG—blood glucose) to certain meals to a profiled healthy response to the same meals and providing an appropriate pre-established tailored bolus delivery pattern in subsequent meals of the same type. The tailored bolus delivery pattern can be selected from a plurality of pre-established bolus delivery patterns, with each pattern allocated to a different GI range (GI—glycemic index). The user can accept a recommended bolus delivery pattern and have a bolus dose delivered accordingly. In some embodiments, the selected bolus delivery pattern may be delivered without acceptance by the user. For example, the user can be notified prior to bolus dose delivery and can suspend the delivery or select an alternative bolus delivery pattern.

Document US 2003/0036927 A1 discloses a record explorer for a healthcare information system that includes a user interface and a search engine. The user interface includes an input device and an output device. The input device is adapted to receive search criteria related to a patient record. The output device is adapted to provide search results responsive to receiving the search criteria. The search engine is adapted to perform a search responsive to receiving the search criteria to generate search results. a user accesses a record explorer, having a user interface and a search engine, from a clinical desktop of a client device. The user selects a patient on which to perform a search. The record explorer presents a series of search criteria on separate tabs with sub-elements for the user to select and build criteria for the search related to the patient's record. For example, the user may select from a list of document types, visits, problems, content definitions, care plans, and healthcare organization as a basis for the search. As the user selects the items for the search, a criteria statement is created and displayed so users can see selected search criteria. Alternatively, the user may use just the contents tab and perform a keyword search to find explanations for clinical terms. In particular a file icon provides the user with access to a selection of searches stored by file name. The favorite searches menu provides the user with access, via a drop down menu, to predetermined stored search criteria that the user frequently uses. After the user initiates the search, the record explorer displays the search results as a list of documents or objects that meet the search criteria. The user selects those items the user wants to view. The user can select each item separately or in a filtered view where all selections are listed at once. If the user has the appropriate privileges, the user may view or update the documents or objects.

Document US 2009/0147011 A1 discloses a system and method for displaying data. The computing device contains data, and has an output device, and may comprise one or more input devices for registering user inputs. The programs generate screen displays incorporating display objects and can process a variety of user inputs. Display objects can be activated by registration of user inputs corresponding to display objects to cause performance of some action within the computing device. The display objects represent data which may be categorized in various ways. A program compares data points and identifies groups of data points located near to each other ("near points") according to predefined or interactively determined criteria. In particular a screen display shows a summary view of a patient's data comprising a primary menu having display objects representing menu items titled summary, patient profile, logbooks and records, graphs, and favorite reports; a secondary menu having display objects representing a plurality of functions such as change patient, print (icon depicting a printer), e-mail (icon depicting an envelope), etc.; a patient identification area for displaying patient identification data; an options bar for changing the display options; a first graph labeled "Standard Week—bG—All" for displaying medical data, and a partial view of a second graph labeled "Insulin Pump Use."

Document US 2013/0164718 A1 discloses a handheld diabetes management device which supports pre-selected meals for improved therapy. By pre-planning meals, an amount of insulin to be delivered to a patient shall be adapted. A user selects food items from a list, for example a favorite list, in order to plan a meal. Pre-defined meals or individual food items may be selected for specifying a pre-planned meal. Based on nutritional information of the pre-planned meal, a bolus calculator suggests a bolus to be delivered to a patient. Favorite food items can be grouped based on preferences of the user. It is further disclosed that food items are removed from a food data base due to an allergy.

Document US 2014/0188398 A1 discloses a methods and an apparatus for remote monitoring. The method includes receiving, at a remote monitor, a notification message representative of an event detected, by a server, from analyte sensor data obtained from a receiver monitoring an analyte state of a host; presenting, at the remote monitor, the notification message to activate the remote monitor, wherein the remote monitor is configured by the server to receive the notification message to augment the receiver monitoring of the analyte state of the host; accessing, by the remote monitor, the server, in response to the presenting of the notification message; and receiving, in response to the accessing, information including at least the analyte sensor data.

SUMMARY

It is an object of the present disclosure to provide a method for providing a favorite menu on a computing device and a computing device in order to simplify the usage of the computing device.

According to aspects of the present disclosure, a method for providing a favorite menu on a computing device and a computing device according to the independent claims are provided. Further embodiments are the subject of dependent claims.

According to one aspect, a method for providing a favorite menu on a computing device is provided. The method comprises steps of: providing an item, wherein at least one action is assigned to the item, storing the item in a favorite list, and displaying the favorite list on a display device of the computing device. The item is provided based on a medical selection criterion.

According to another aspect, a computing device is provided. The computing device comprises a processor, a memory, and a display device. The processor is configured to provide an item, wherein at least one action is assigned to the item, store the item in a favorite list, and display the favorite list on the display device. The item is provided based on a medical selection criterion.

The method provides a favorite menu (favorite list) with one or more items, wherein each item is assigned to an action. This allows quick and customizable access to specific features and actions. The list of items is based on a medical selection criterion to simplify menu handling for the user. As such, the favorite list may include item assigned to a defined set up of actions, in particular medical actions.

The computing device may be a portable computing device, for example a mobile phone, a smartphone or a tablet PC. The display device of the computing device may be a touch sensitive screen configured to receive user input.

In one embodiment, a first list comprising several pre-defined items may be provided. At least one of the pre-defined items may be selected from the first list based on the medical selection criterion, and the at least one selected pre-defined item may be stored in the favorite list.

The pre-defined item may be adapted by assigning a further action to the pre-defined item and/or removing an existing action from the pre-defined item before storing the adapted item in the favorite list. A user shall see what he expects. The items can be adapted to refer to individual standard tasks of the user. The user may select items referring to previous actions he has performed before to reuse them again as an immediate action trigger, by making them a favorite instance. The computing device may be configured to provide a review of all recent actions, e.g. performed during the last TBD day (TBD-total basal insulin dose). The items having the highest value to the user may be selected for adding them to the favorite list.

In another embodiment, the item may be generated by assigning at least one action to the item and stored in the favorite list. The item may be generated based on the medical selection criterion. This embodiment refers to creating an item from scratch. If an item is created from scratch, it may be generated from a food library or a bolus workflow. The item may comprise an action which shall be performed in future time. For example, a starting time may be provided for a TBR reduction (TBR-temporal basal rate) of a specific amount (X %) for a specific duration. This allows a pre-programming of an appropriate TBR reduction in the night following expected alcohol intake before going to a restaurant or a bar. Similar applies for sport events. The possibility of a "one-click" activation from the favorite list promotes using such safety tools in a very convenient way at a time when it is possible to care about the right insulin adaption.

By adapting a pre-defined item or by generating a new item from scratch, several actions may be grouped in the item.

The medical selection criterion may relate to a complexity of a medical action, a clinical value of the medical action or a criticality of the medical action. With regard to the complexity criterion, the favorite list may list complex actions such as extended or multi wave bolus actions which the user frequently uses. With regard to the clinical value criterion, the favorite list may list actions that the user frequently uses and has proven to keep the users BG level in target. With regard to the criticality criterion, the favorite list may list actions that are critical to the users BG level (bolus, carbs).

The action may refer to a control command for the computing device or to a further control command for a medical device coupled to the computing device. The further control command may be transmitted from the computing device to the medical device. The medical device may be connected to the computing device via a wired or wireless connection. The wireless connection may be established via WLAN, Wi-Fi or Bluetooth. The medical device may be an insulin pump. The further control command may be configured to control an insulin delivery by the insulin pump. Controlling insulin delivery may comprise controlling an amount of insulin dispensed by the insulin pump and/or controlling a time/duration of insulin delivery. For example, a command for dispensing a TBR may be generated by the computing device and transmitted to the insulin pump.

An item may be assigned to one or more actions. A plurality of control commands for the computing device and/or for the medical device may be grouped in a single item. This allows quick access of a user to complex tasks.

The actions may comprise control commands for insulin delivery (basal and bolus), carb-entries, BG testing as well as event management (health events, activity). The actions may be selected from the following actions: single meal items (e.g. a snack like Snickers), complex meals (e.g. a standard cantina menu), insulin delivery (e.g. 4 U standard bolus or extended bolus, 5.5 U for 3:00 hours), activation of temporary basal rate (e.g. 90% for 1:50 hours), health event (e.g. illness, accident), exercise event (e.g. sports activity), basal profile change (e.g. "weekend" vs "weekday" profile), and adding a note with a pre-entered text. The actions may further comprise a command to stop the insulin pump, enter a manual bolus, add a note, or search for a specific food.

The item stored in the favorite list may enable execution of the action assigned to the item without further user input. This may also be called "one-click" action and enables quick selection of actions relevant for different life style situations, for example activating a standard TBR for jogging three times a week, activating a flight mode of the computing device for frequent travelers, or eating always the same when going to a fast food restaurant.

The item stored in the favorite list may enable execution of the action assigned to the item after receiving a confirmation, e.g. by user input. Before receiving confirmation, the action assigned to the item may be modified. If a complex meal (comprising a burger, fries, a coke and a dessert) is stored as favorite, it may be selected with a first user input. With a second user input, the selection can be confirmed or modified before confirmation. For example, the fries may be deleted from the meal.

The favorite list may be accessible by a specific user input, e.g. by sliding vertically over the display device in order to access the favorite list. From an unlock screen of a touch screen device (e.g. a smartphone or a tablet) direct access to the favorite list may be possible.

The favorite list may be accessible on the computing device even if other operations of the computing device are locked. Operation in so called "children's use case" allows a mother to prepare food (e.g. for the kindergarden) and store all items as favorites in the first list together with a picture. The items may comprise bread, apple, and yoghurt, for example. A child, which is able to recognize the food but is not yet able to do carb calculations, can only access the items in the favorite list. The child may press on the item "apple" if it decides to eat an apple. The computing device will provide the right insulin amount. In the evening, the mother may delete the favorites and program new favorites for the next day according to the food she prepares. The item may be provided as a graphical item comprising a picture. The graphical item may be assigned to an action, e.g. a control command for an insulin pump connected to the computing device to deliver a specific amount of insulin. The item may also be assigned to complex actions, e.g. delivering a specific amount of insulin at a specific time and for a specific duration.

The favorite list may be provided with selected read permission and/or selected write permission for different users, e.g. for parents and kids. The parent may set up the favorite list (e.g. selected food items including carbs) and the kid may only access the items of the favorite list without modifying them.

Making the items easily accessible in a favorite list may increase the users overall satisfaction from the system, by introducing customization. The user may be exposed to features which are "hidden" in the computing device. The method may make it easier for the user to quickly respond to diabetes conditions by elements he has used before, reducing complexity and improving overall diabetes management. Interaction between parents and children may be facilitated and responsibility for diabetes self-management in children may be increased.

DESCRIPTION OF FURTHER EMBODIMENTS

Figure 2:
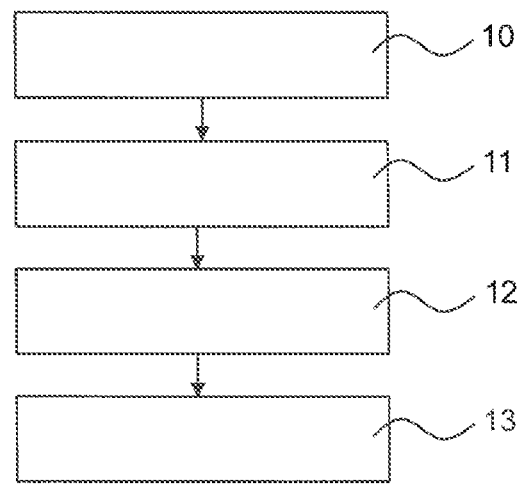
Figure 3:
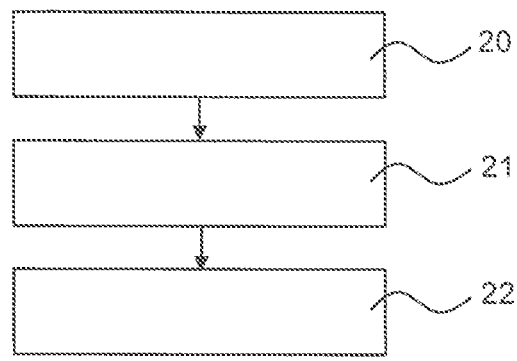
Figure 4:
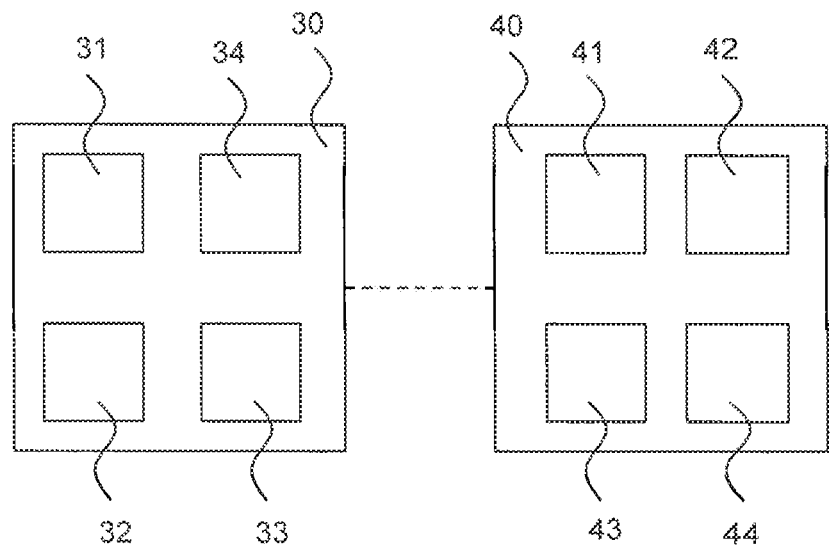
Figure 5:
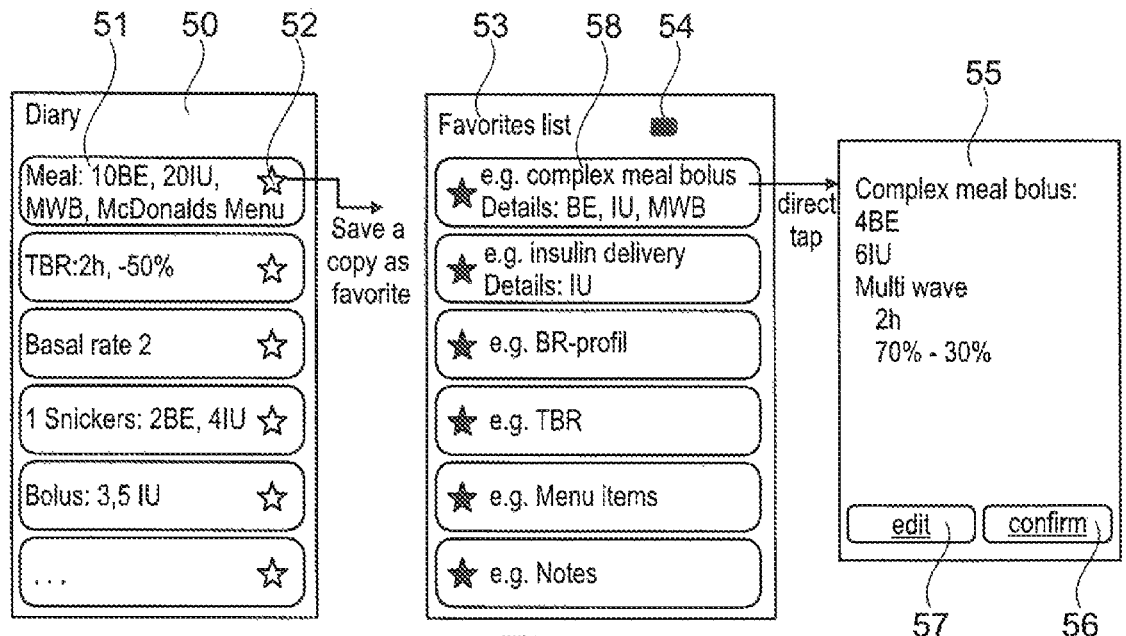
Figure 6:
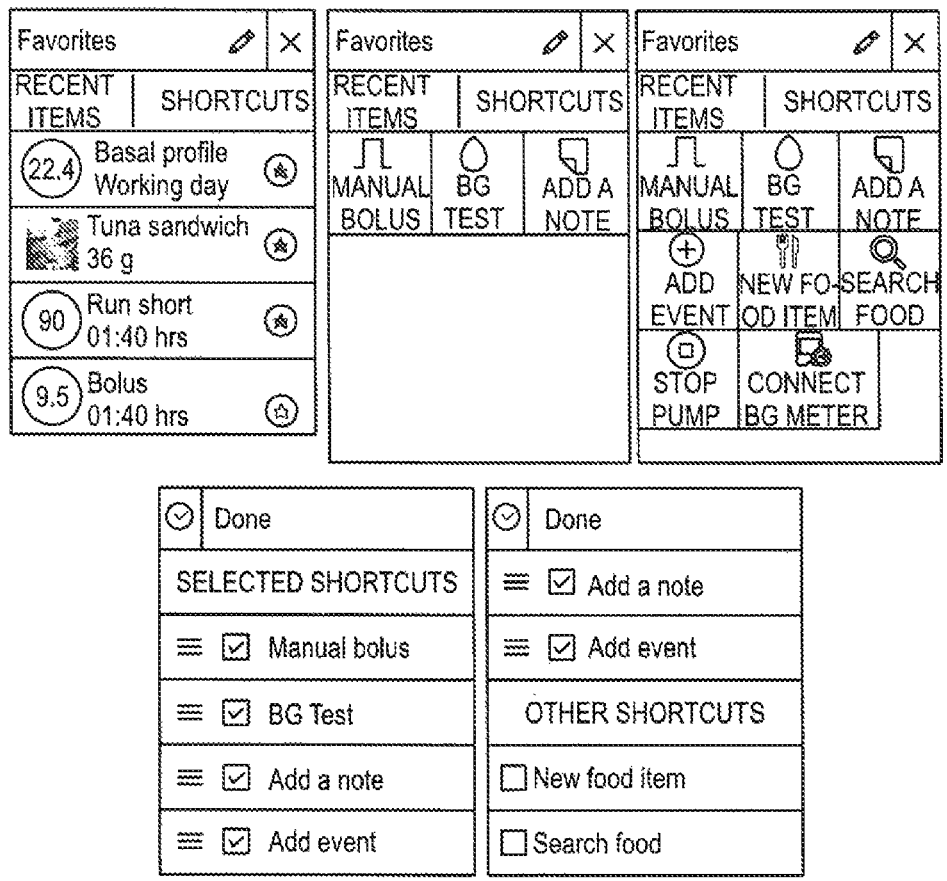

Following, further embodiments are described with reference to figures. In the figures, show:

FIG. 1 is a schematic block diagram of a method for providing a favorite menu, FIG. 2 is a schematic block diagram of another method for providing a favorite menu, FIG. 3 is a schematic block diagram of a further method for providing a favorite menu, FIG. 4 is a schematic block diagram of a computing device and a medical device, FIG. 5 shows an embodiment of a favorite menu, and FIG. 6 shows further embodiments of a favorite menu.

FIG. 1 shows a schematic block diagram of a method for providing a favorite menu. First, an item is provided (step 1). At least one action is assigned to the item. The item is provided based on a medical selection criterion. The item is stored in a favorite list (step 2). Then, the favorite list is displayed on a display device of a computing device (step 3).

FIG. 2 shows a schematic block diagram of another method for providing a favorite menu. In step 10, a list comprising several pre-defined items is provided. Next, at least one of the pre-defined items is selected from the list (step 11). The selection is based on a medical selection criterion. The selected item is stored in a favorite list (step 12). The favorite list is displayed on a display device of a computing device in step 13. The selected item may be modified before storing it in the favorite list.

FIG. 3 shows a schematic block diagram of a further method for providing a favorite menu. In step 20, a new item is created by assigning at least one action to the item. The creation is based on a medical selection criterion. The new item is stored in a favorite list (step 21) which is displayed on a display device (step 22).

FIG. 4 shows a schematic representation of a computing device 30 coupled to a medical device 40. The computing device 30 comprises a processor 31, a memory device 32, a display device 33 and a communication device 34. The processor 31 is configured to provide a favorite list according to the steps disclosed herein. The favorite list may be stored in the memory device 32 and shown on the display device 33. A connection to the medical device 40 is established via the communication device 34. The medical device 40 comprises a further processor 41, a further memory device 42, a further communication device 43 and an insulin delivery device 44. The medical device 40 may be an insulin pump. The medical device 40 may receive control signals from the computing device via the further communication device 43. The further processor 41 may be configured to control insulin delivery by the insulin delivery device 44 based on the received control signals.

In FIG. 5 an embodiment of a favorite menu is shown. A first list 50 is shown on the left side of FIG. 5. The first list 50 comprises several items 51 referring to actions of diabetes management. A button 52 is provided. By activating the button 52, a selected item is stored in a favorite list 53. The favorite list 53 comprises a filter button 54 for filtering the items. A favorite item 58 of the favorite list 53 may be selected by tapping on the favorite item 58. This opens a new window 55 in which details of the selected favorite item are shown. The window 55 comprises a confirmation button 56 and an edit button 57. Pushing the confirmation button 56, a user accepts the selected item without changes. Hereby, a user can activate the favorite item 58 with only two user interactions, namely selection and confirmation. Alternatively, the selected favorite item may be adapted to a specific situation by pushing the edit button 57.

FIG. 6 shows further embodiments of graphical user interfaces of a favorite menu.

The invention claimed is:

1. A method for for controlling a medical device, the method comprising the steps of:
   providing a controller for controlling the medical device, the controller comprising a processor, a memory and a display device;
   providing a first list comprising several pre-defined items, each predefined item being provided based on a medical selection criterion, at least one action being assigned to each pre-defined item, the action being a control command for controlling the operation of the medical device, the action being one that is automatically performed by the controller upon selection of a predefined item, the control command being selected from the group consisting of delivering insulin and stopping an insulin pump;
   selecting using the processor at least one of the pre-defined items from the first list based on the medical selection criterion;
   adapting using the processor the selected pre-defined item to form an adapted pre-defined item by at least one of assigning a further action to the pre-defined item, modifying an existing action of the pre-defined item, and removing an existing action from the pre-defined item;

storing using the processor the adapted pre-defined item in a favorite list, wherein the control command stored in the pre-defined item in the favorite list automatically provides execution of the action assigned to the control command without further user input;

the processor displaying the favorite list on a display device; and selecting the adapted pre-defined item and thereby automatically controlling using the processor the medical device in accordance with the adapted pre-defined item.

2. The method according to claim 1, and which further includes defining a new item, wherein the new item is generated by assigning at least one action to an item stored in the favorite list, and wherein the new item is generated based on a medical selection criterion.

3. The method according to claim 1, wherein the medical selection criterion relates to a complexity of a medical action, a clinical value of the medical action, or a criticality of the medical action.

4. The method according to claim 1, wherein the control command is configured to control delivering insulin by an insulin pump.

5. The method according to claim 1, wherein the favorite list is accessible on a computing device even if other operations of the computing device are locked.

6. The method according to claim 1, wherein the favorite list is provided with at least one of selected read permission and selected write permission for different users.

7. A computing device for providing and adapting a favorite list of selected action items and for controlling a medical device, the computing device comprising:

a processor;
a memory; and
a display device,
wherein the processor:
provides a first list comprising several pre-defined items, each pre-defined item being provided based on a medical selection criterion, at least one action being assigned to each pre-defined item, the action being a control command for the medical device, the control command being selected from the group consisting of delivering insulin and stopping an insulin pump, selects at least one of the pre-defined items from the first list based on the medical selection criterion, adapts the selected, pre-defined item to form an adapted, pre-defined item by at least one of assigning a further action to the pre-defined item, modifying an existing action of the pre-defined item, and removing an existing action from the pre-defined item before storing the adapted, predefined item in the favorite list, stores the adapted, pre-defined item in a favorite list, wherein the control command stored in the adapted, pre-defined item in the favorite list automatically provides execution of the action assigned to the control command without further user input, displays the favorite list on the display device, and
controls the medical device in accordance with the adapted pre-defined item.

* * * * *